(12) United States Patent
Zhang et al.

(10) Patent No.: US 7,556,828 B2
(45) Date of Patent: Jul. 7, 2009

(54) PHARMACEUTICAL COMPOSITION FOR TREATMENT OF BPH AND PREPARATION THEREOF

(76) Inventors: Zuguang Zhang, Rm 406, Tower B, Jia Run Garden, Wangjing Chaoyang District, Beijing (CN); Yufen Wang, Rm 302, 4th Entrance, No. 4 Building Hou Tai Bi Xuan Yuan, West Fu Kang Road, Nan Kai District, Tianjin (CN) 300191

( * ) Notice: Subject to any disclaimer, the term of this patent is extended or adjusted under 35 U.S.C. 154(b) by 0 days.

(21) Appl. No.: 10/515,910

(22) PCT Filed: Apr. 4, 2003

(86) PCT No.: PCT/CN03/00243

§ 371 (c)(1),
(2), (4) Date: Nov. 24, 2004

(87) PCT Pub. No.: WO2004/084924

PCT Pub. Date: Oct. 7, 2004

(65) Prior Publication Data

US 2005/0220904 A1  Oct. 6, 2005

(30) Foreign Application Priority Data

Mar. 28, 2003  (CN)  ............... 03 1 21170 A (51) Int. Cl.
| A61K 36/254 | (2006.01) |
|---|---|
| A61K 36/258 | (2006.01) |
| A61K 36/16 | (2006.01) |
| A01N 65/00 | (2006.01) |
| A61K 36/54 | (2006.01) |
| A61K 36/48 | (2006.01) |
| A61K 36/00 | (2006.01) |

(52) U.S. Cl. ............ 424/725; 424/728; 424/752; 424/739; 424/757

(58) Field of Classification Search ............ None
See application file for complete search history.

(56) References Cited

U.S. PATENT DOCUMENTS

| 5,595,743 | A | * | 1/1997 | Wu | 424/728 |
| 5,942,233 | A | * | 8/1999 | Chang | 424/758 |
| 6,197,309 | B1 | * | 3/2001 | Wheeler | 424/727 |
| 2001/0000144 | A1 | * | 4/2001 | Keller et al. | 424/728 |

FOREIGN PATENT DOCUMENTS

| CN | 1088442 A | * | 6/1994 |
| CN | 1159933 A | | 9/1997 |
| CN | 98113889.6 | | 10/1999 |
| JP | 09249576 A | * | 9/1997 |
| JP | 09315930 A | * | 12/1997 |
| JP | 10072336 A | * | 3/1998 |
| JP | 11137232 A | * | 5/1999 |
| JP | 11137232 A | * | 5/1999 |
| KR | 910007606 B | * | 9/1991 |
| KR | 950013026 B | * | 10/1995 |

OTHER PUBLICATIONS

Zongde, N. Abstract. Application No. 00119396, Publication No. 1333037, Publication Date: Jan. 30, 2002.*
Myhre, Herbal Remedies, Nephropathies and Renal Disease, Nephrol. Nurs. J., vol. 27, No. 5 (Oct. 2000) pp. 473-480, PubMed abstract.*
Scott et al. Update on natural product-drug interactions. Am J Health Syst Pharm, vol. 59, No. 4 (Feb. 2002) pp. 339-347, PubMed abstract.*
Grieve, Mrs. M. 'Cassia (Cinnamon)'. Botanical.com: A modern herbal. Feb. 28, 1997 [retrieved on Sep. 18, 2007] URL<http://web.archive.org/web/*/http://botanical.com/botanical/mgmh/c/cassia31.html> p. 1.*
China Pharmacy 13(2), pp. 112-113, (2002), Jiang, H., et al. "Medicine for the Treatment of Benign Prostate Hyperplasia".

* cited by examiner

Primary Examiner—Christopher R Tate
Assistant Examiner—Amy L Clark
(74) Attorney, Agent, or Firm—Hedman & Costigan, P.C.

(57) ABSTRACT

A pharmaceutical composition with higher curative effect on benign prostate hyperplasia and emiction disorders. It uses plants such as ginseng and ginkgo as well as cassia twig, cinnamon and liquorices as raw materials in both food and medicine. These raw materials are decocted or extracted separately in ethanol solution or water, then concentrated and dried to make the said pharmaceutical composition. Because this pharmaceutical composition is not toxic and has no side effect, it can be prepared as a medicament and health food to treat and improve benign prostate hyperplasia and emiction disorders caused by benign prostate hyperplasia.

6 Claims, 3 Drawing Sheets

PHARMACEUTICAL COMPOSITION FOR TREATMENT OF BPH AND PREPARATION THEREOF

TECHNICAL FIELD

This invention relates to a pharmaceutical composition for the improvement and treatment of emiction and urinary disorders caused by benign prostate hyperplasia (BPH). It can be used as a treatment or as a preventative measure.

This invention also relates to methods of preparing the pharmaceutical composition.

BACKGROUND OF THE INVENTION

The emiction disorder caused by benign prostate hyperplasia (BPH) is a familiar and frequently-occurring disease that harms and distresses the health of both elderly and middle-aged men. With the increasing age of the population in recent years, the rate of emiction disorders has been on the rise. For example, almost one third of American adult men have BPH diseases. In China, the incidence of BPH is also on the rise: in 1936, the rate of BPH in Chinese men over the age of 41 was about 6.6%; as of the last known figures, the rate in the same population is 30.5%.

The modern medical studies have proven that there are two factors leading to lower urethra hamperness caused by prostate hypertrophy: (1) dynamic factors and (2) static factors. At present, two major categories of medicaments are used clinically to treat BPH: (1) α-1-adrenal receptor blocking agents and (2) 5-α-reductase inhibitor (antiandrogen). The α-1-adrenal receptor blocking agent acts to reduce tension on the smooth muscles of the prostate gland and on the neck of the bladder. Thus, the dynamic factor (i.e., blockage of the bladder) is released to abate or remove the clinical symptoms. Representative of the α-1-adrenal receptor blocking agents are HARNA, TERAZOSIN, etc. The 5-α-reductase inhibitor inhibits BPH by stopping testosterone from being transformed into dihydrotestosterone (DHT). Representative of the 5-α-reductase inhibitor is PROSCAR. While both types of medicaments are effective, there are side effects.

There are also compounds used to treat BPH that are formulated from pure plants. Exemplary of these medicaments are CEFASABAL (which includes extracts of *sabalis serrulatae fructus, solidaginis herba* and *hippocastani semen*) and PROSTAT (which includes water-soluble pollen extract P5 and fat-soluble pollen extract EA10) pollen preparations. While there do not seem to be side effects with these pure plant compounds, they are not quick-acting, and long periods of treatment are required.

In the realm of traditional Chinese medicine, the emiction disorder caused by BPH belongs to the joint categories of dysuria and blockage. "Dysuria" refers to difficult in urination, a slim and fragile urine line and blocked urine. When urination occurs with a degree of difficultly, it is referred to as "dysuria". When urination cannot occur, it is referred to as being blocked (i.e., the patient is suffering from "blockage"). Traditional Chinese medicine treats BPH with a compound that can be considered to target multiple parts of the body. Advantageously, patients are safely treated with a whole-body treatment. However, it suffers from the same drawbacks as the pure plant compounds.

Chinese Patent No. 98113889.6 describes a kind of capsule and its preparation method. In the method, raw materials (such as rough gentian, dried rehmannia root, Tuckahoe, celery wormwood, root of Chinese thorowax, tulip, cordate houttuynia and devilpepper) are soaked in 8-fold water for 2 hours, the raw materials are then removed and the water is collected. Next, the raw ingredients are soaked in 5-fold water for 1 hour, the raw materials are then removed and the water is collected. Next, the raw materials are soaked in 3-fold water for 1 hour, the raw materials are removed and the water is collected. The three collections of water are combined, decompressed, and concentrated as a dry extract. The dry extract is then comminuted (crushed) and encapsulated. This preparation is believed to: clear away evil heat and expel superficial evils; relieve rheumatic pains; cure colds; reduce swellings, relax the liver; dispell melancholy; and increase blood circulation in order to dissipate blood stasis. It can be used to treat diseases such as acute and chronic prostatitis, prostate hypertrophy, etc. The preparation has obvious curative effects, and the symptoms of dysuria are obviously improved. The efficacy rate can reach 90%. However, the side effects can be relatively complicated, especially with uncertain effects on emiction disorders.

SUMMARY OF THE INVENTION

In order to overcome the shortcomings in the prior art, the object of this invention is to provide a pharmaceutical composition for the improvement and treatment of emiction disorders caused by benign prostate hyperplasia (BPH). The invention is formulated from plants and can be used both as a medicament and as a health food.

Another object of the invention is to provide a medicament and health food that has no noxious side effects and that can be taken over the long-term as a medicament for treatment of BPH emiction disorders.

Another object of the invention is to provide a health food that can slow the aging process.

By combining Chinese medicine with modern medicine, a treatment for BPH has been created that is based on plant extracts. The treatment is for the improvement of emiction disorders caused by BPH. The treatment is safe and has a strong quick-acting curative effect, sometimes taking as little as a week before the effects are experienced. When taken for an extended period of time, the treatment can boost the immune system and slow the aging process.

Another object of the invention is to provide a method of preparing the above-mentioned pharmaceutical composition.

These and other objects are realized by the composition of the present invention.

In a first preferred embodiment, the composition comprises 9-45 parts by weight of root of *Panax ginseng* C.A. Mey and 20-100 parts by weight of *Ginkgo biloba* L., preferably 18-36 parts by weight of *Panax ginseng* C.A. Mey and 40-80 parts by weight of seed of *Ginkgo biloba* L. based on the weight ratio. Even more preferably, the composition comprises 27 parts by weight of *Panax ginseng* C.A. Mey and 60 parts by weight of seed of *Ginkgo biloba* L.

In a second preferred embodiment, 2-30 parts by weight of *Cinnamomum cassia* Presl and 2-10 parts by weight of licorice (root of *Glycyrrhiza uralensis* Fisch) are included in the above-described composition. This second preferred embodiment enhances the anti-inflammatory and inhibitive effects on prostate hypertrophy.

In a third preferred embodiment, 6-12 parts by weight of twig of *Cinnamomum cassia* Presl are added to the second preferred embodiment. This third preferred embodiment strengthens the diuretic effect of the pharmaceutical composition.

The pharmaceutical composition of the present invention optionally further comprises pharmaceutically acceptable carriers or additives. The composition can be in any suitable form, however preferred is a powder or tablet.

The preferred method of preparing the composition is:

1. soaking and extracting 9-45 parts by weight of *Panax ginseng* C.A. Mey in ethanol or water, followed by separation and purification by means of chromatography and drying to create a first extract;
2. soaking and extracting 20-100 parts by weight of seed of *Ginkgo biloba* L. in ethanol or water, followed by separation and purification by means of chromatography and drying to create a second extract;
3. mixing the first extract and the second extract to create a mixed extract, followed by crushing and sieving the mixed extract in order to obtain the final extract—the present invention.

In the preferred method, 18-36 parts by weight of *Panax ginseng* CA. Mey and 40-80 parts by weight of seed of *Ginkgo biloba* L. are more preferred, and 20 parts by weight of *Panax ginseng* C.A. Mey and 60 parts by weight of seed of *Ginkgo biloba* L. are even more preferable.

In the preferred method, it is also envisioned that 2-30 parts by weight of bark of *Cinnamomum cassia* Presl and 2-10 parts by weight of licorice can also be soaked and extracted.

In the preferred method, it is also envisioned that 6-12 parts by weight of twig of *Cinnamomum cassia* Presl can also be soaked and extracted.

In a second preferred method, 9-45 parts by weight of *Panax ginseng* CA. Mey, 20-100 parts by weight of seed of *Ginkgo biloba* L., 6-12 parts by weight of twig of *Cinnamomum cassia* Presl, 2-30 parts by weight of bark of *Cinnamomum cassia* Presl and 2-10 parts by weight of licorice are dedocted in water or ethanol solution to obtain separate extracts. The separated extracts are concentrated separately in order to obtain individual pastes. The pastes are dried separately to obtain the water or ethanol extracts. The extracts are then mixed together and crushed.

It is well known by those of skill in the art that the raw materials used in the invention can have extracts made by any known method. The composition that is created after the extracts are dried, crushed, sieved and mixed has surprisingly been shown to be effective in the treatment of patients suffering from emiction disorders caused by BPH.

According to the present invention, either ginseng (*Panax gineng* C. A. Mey) and/or the rootstock of *Panax ginseng* C.A. Mey can be used. According to different processing methods, the medical/commercial garden ginsengs, also called seedling ginsengs, include red ginseng, strake ginseng, sugar-dipped ginseng, white ginseng, sun-dried ginseng, sun-cured white ginseng root, nipped ginseng and Dali ginseng. Any of these ginsengs can be used in the compositions and methods of the present invention. Additionally, the compositions and methods of the present invention can include wild ginseng, migrated ginseng, Korean ginseng and Korean red ginseng.

The part of ginkgo (*Ginkgo biloba* L.) useful in this invention is the dried seed without the crust.

The cassia twig is the young twig of the *Cinnamomum cassia* Presl.

The cinnamon is the dried tree or twig bark of the *Cinnamomum cassia* Presl.

The licorice is the root and root-shaped stem of the *Glycyrrhiza uralensis* Fisch.

The pharmaceutical composition or extracts of this invention can be used to make healthy food or food complements.

The pharmaceutical composition or extracts of the present invention have the following features and advantages:

1. The raw materials are all natural edible plants. All the components comply with the regulations of the "Management Methods of Healthy Food" and the "Medicine Act" of the People's Republic of China (PRC). The components have no toxic side effects. They have also been shown to be safe for long-term consumption.
2. Signs of improvement in a patient can sometimes be seen after only a week. Long-term effects include boosting immunity and slowing the aging process.
3. The pharmaceutical compositions have the potential for further development of various types of products (e.g., food, health food and medicaments).

DETAILED DESCRIPTION OF THE DRAWINGS

In combination with the FIGS. 1, 2 and 3, the present invention is explained in detail as follows.

Example 1

Figure 1:
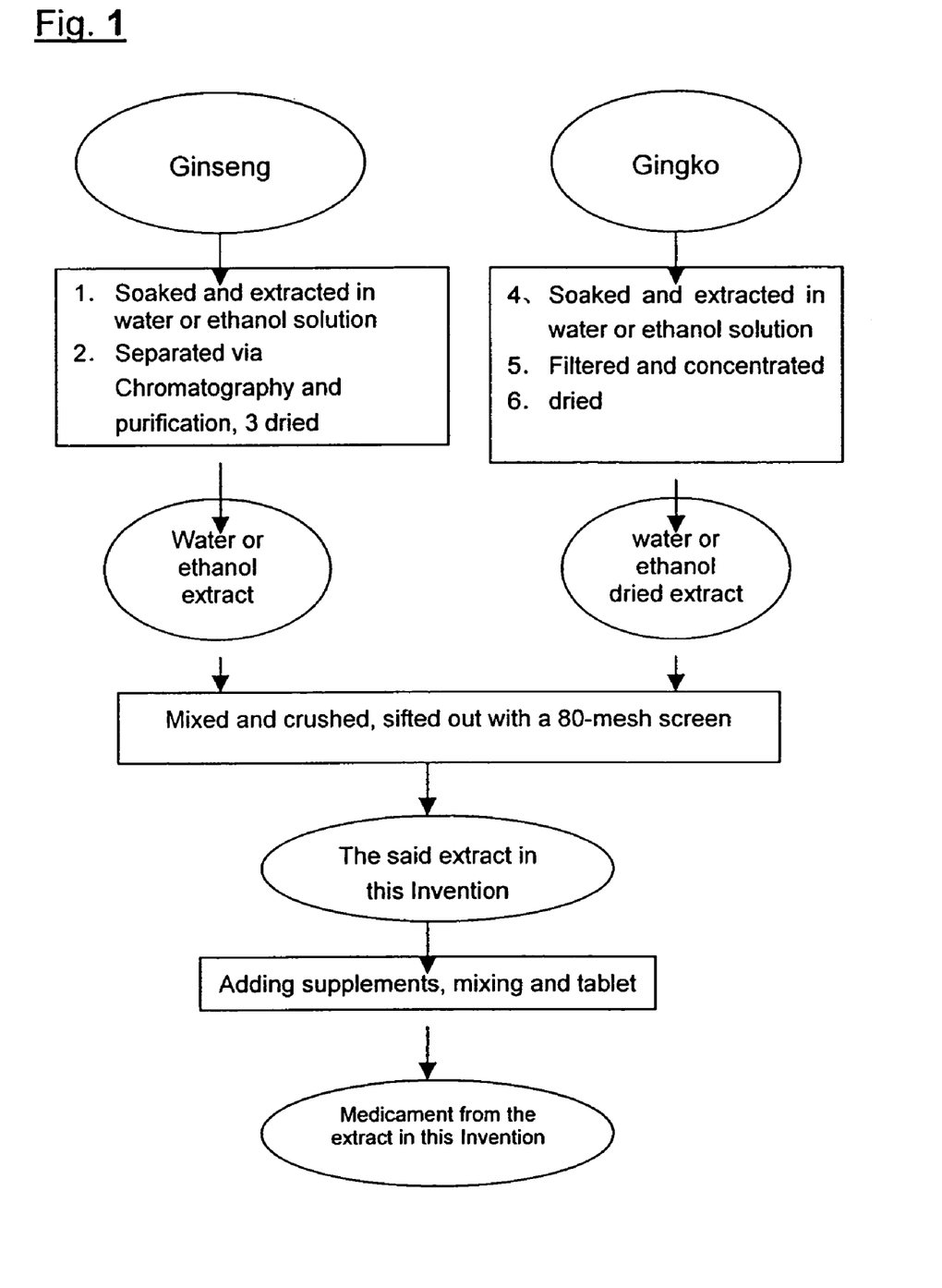
FIG. 1 is a flow chart depicting one method of creating the extract of the present invention.
Figure 2:
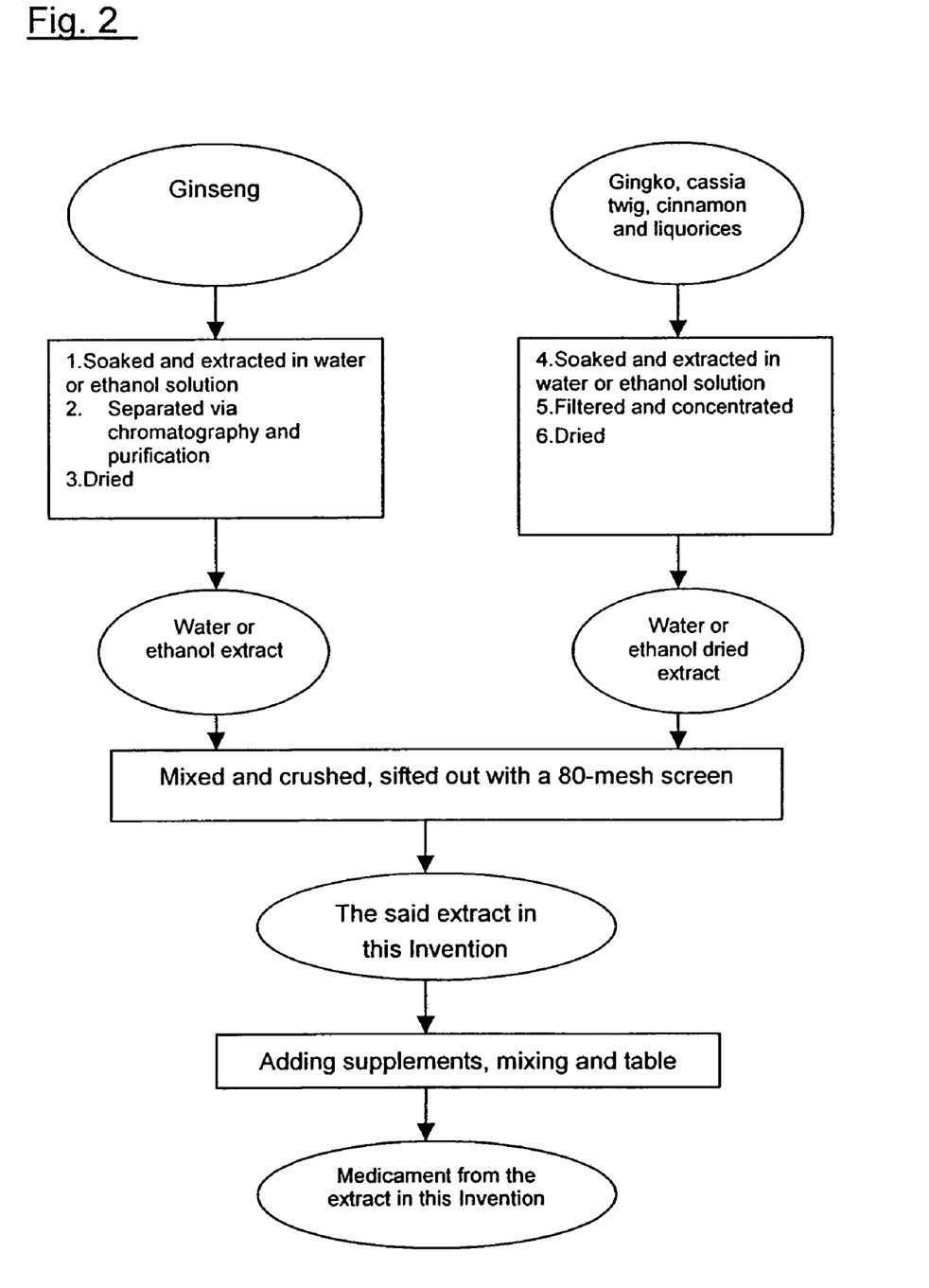
FIG. 2 is a flow chart depicting a second method of creating the extract of the present invention.

As best shown in FIG. 1, 27 kg of *Panax ginseng* C.A. Mey were soaked and extracted in 70% ethanol solution. The solution was then chromatographed, purified and dried to obtain the ethanol extract. 60 kg seed of *Ginkgo biloba* L. were soaked and extracted in water, filtered, concentrated and dried to obtain water dry extracts. The ethanol extract and water dry extract were mixed together and crushed, and then sifted with an 80-mesh screen to obtain the final extract.

Example 2

The procedure in Example 1 was repeated except that 9 kg of *Panax ginseng* C.A. Mey and 20 kg of seed of *Ginkgo biloba* L. were soaked and extracted in an ethanol solution separately.

Example 3

The procedure in Example 1 was repeated except that 45 kg of *Panax ginseng* C.A. Mey and 100 kg seed of *Ginkgo biloba* L. were decocted in water separately.

Example 4

As best shown in FIG. 1, 27 kg of *Panax ginseng* C.A. Mey were soaked and extracted in 70% ethanol solution. The solution was then chromatographed, purified and dried to obtain an ethanol extract. 60 kg of seed of *Ginkgo biloba* L., 3 kg bark of *Cinnmomum cassia* Presl, 3 kg of licorice and 9 kg of twig of *Cinnmomum cassia* Presl were decocted in water, filtered, concentrated and dried to obtain dry water extracts.

The ethanol extract and dry water extracts were mixed together and crushed, and then sifted with a 80-mesh screen to obtain the final extract. The final extract was then encapsulated by methods known to persons skilled in the art.

Example 5

The procedure in Example 4 was repeated except that 45 kg of *Panax ginseng* C.A. Mey, 100 kg seed of *Ginkgo biloba* L., 2 kg of bark of *Cinnmomum cassia* Presl, and 2 kg of licorice were extracted in ethanol solution or water separately. The extracts were then mixed together and crushed to obtain the final extract.

Example 6

The procedure in Example 4 was repeated, except that 9 kg of *Panax ginseng* C.A. Mey, 20 kg of seed of *Ginkgo biloba* L., 30 kg bark of *Cinnmomum cassia* Presl, and 10 kg of licorice were extracted in ethanol solution or water separately. The extracts were then mixed together and crushed to obtain the final extract. The final extract was then made into a powder by methods known to persons skilled in the art.

Example 7

The procedure in Example 6 was repeated except that 12 kg of twig of *Cinnmomum cassia* Presl was also extracted in ethanol solution or water. This extract was then mixed with the extracts from Example 6, and the mixture was then crushed to obtain the final extract.

Example 8

The procedure in Example 5 was repeated except that 6 kg of twig of *Cinnmomum cassia* Presl was also extracted in ethanol solution or water. This extract was then mixed with the extracts from Example 5, and the mixture was then crushed to obtain the final extract.

Example 9

Figure 3:
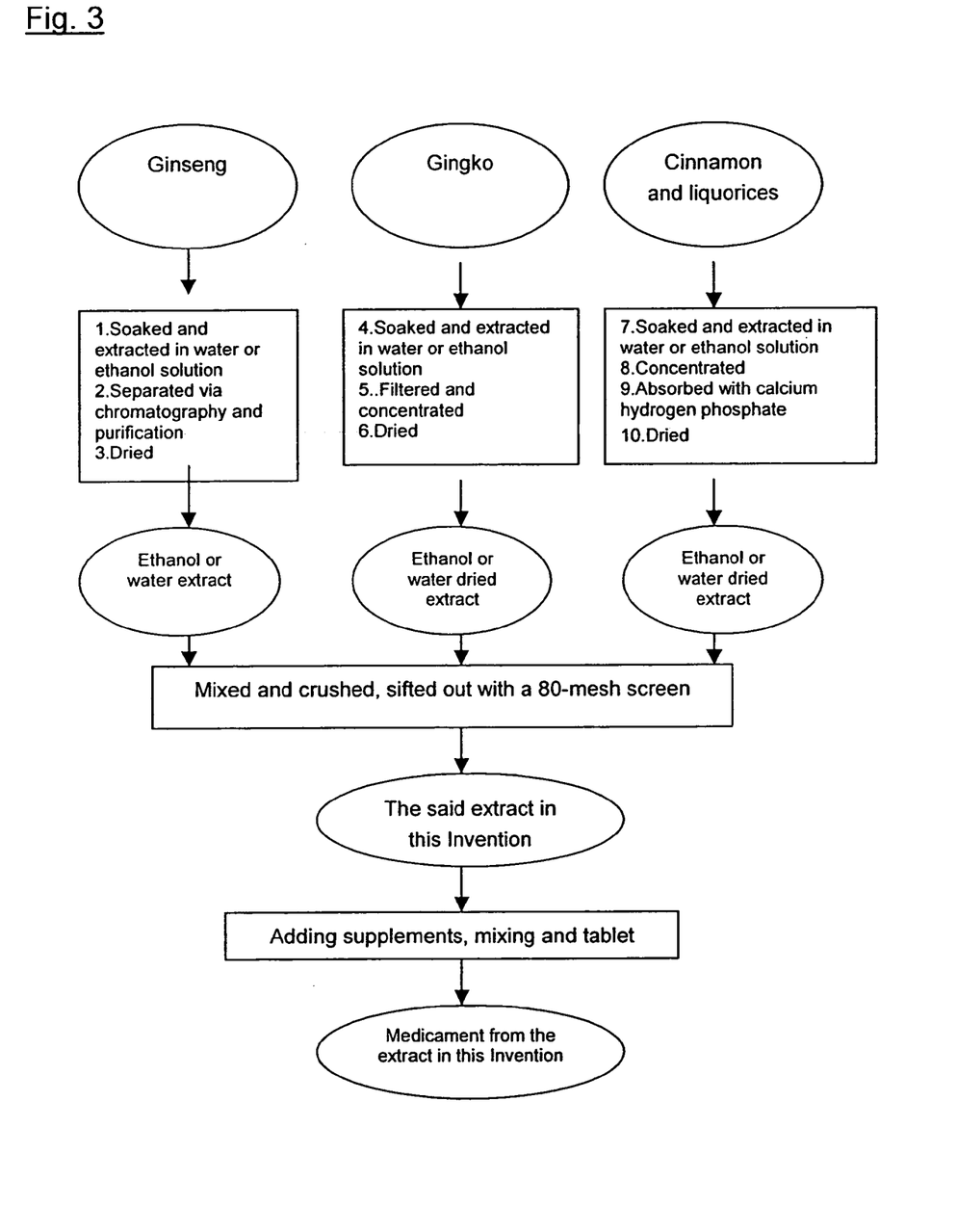
FIG. 3 is a flow chart depicting a third method of creating the extract of the present invention.

As best shown in FIG. 3, 27 kg of *Panax ginseng* C.A. Mey were soaked and extracted in a 70% ethanol solution. The ethanol solution was chromatographed, purified and dried to obtain an ethanol extract. 60 kg of seed of *Ginkgo biloba* L. were soaked and extracted in water to obtain a water solution. The water solution was then filtered, concentrated, and dried to obtain a dry water extract. The ethanol and dry water extracts were then mixed and crushed to obtain an intermediate extract.

24 kg of bark of *Cinnmomum cassia* Presl and 6 kg of licorice were then mixed and decocted in 95% ethanol solution. This solution was then filtered and concentrated, absorbed with a suitable amount of officinal calcium hydrogen phosphate, and then dried to obtain the dry ethanol extract.

The intermediate extract of *Panax ginseng* C.A. Mey and the dry water extract of seed of *Ginkgo biloba* L. were mixed with the dry ethanol extracts of bark of *Cinnmomum cassia* Presl and licorice, the entire mixture was then crushed and filtered with an 80-mesh screen to obtain the final extract. The final extract was then made into a powder by methods known to persons skilled in the art.

Example 10

The procedure of Example 9 was repeated except that 18 kg of *Panax ginseng* C.A. Mey, 40 kg of seed of *Ginkgo biloba* L., 2 kg of bark of *Cinnmomum cassia* Presl and 2 kg of licorice were decocted and extracted in water to obtain a dry water extract. The dry water extracts of *Panax ginseng* C.A. Mey and ginkgo were dried together with the dry water extracts of bark of *Cinnmomum cassia* Presl and licorice to make the final extract.

Example 11

27 kg of *Panax ginseng* C.A. Mey, 60 kg of seed of *Ginkgo biloba* L., 9 kg of twig of *Cinnmomum cassia* Presl, 3 kg of bark of *Cinnmomum cassia* Presl and 3 kg of licorice were decocted in water or 70% ethanol solution and filtered separately to obtain individual extracts. The individual extracts were then concentrated to obtain dry extracts, and were further dried to obtain their own dry water or ethanol extracts separately. Finally, the obtained dry extracts were crushed and filtered with an 80-mesh screen to be mixed together to obtain the final extract.

Example 12

9 kg of *Panax ginseng* CA. Mey and 20 kg of seed of *Ginkgo biloba* L. were directly crushed and filtered with an 80-mesh screen to obtain the pharmaceutical composition of the present invention. The composition was then pressed and made into tablets according to methods known to those of skill in the art.

Example 13

45 kg of *Panax ginseng* C.A. Mey, 100 kg of seed of *Ginkgo biloba* L., 30 kg of bark of *Cinnmomum cassia* Presl and 10 kg of licorice were directly crushed and filtered with an 80-mesh screen to obtain the pharmaceutical composition of the present invention. The composition was then pressed and made into tablets according to methods known to those of skill in the art.

Example 14

The procedure of Example 13 was repeated except that 12 kg of twig of *Cinnmomum cassia* Presl was added, crushed and sifted out.

Example 15

The procedure of Example 13 was repeated except that 18 kg of *Panax ginseng* C.A. Mey, 40 kg of seed of *Ginkgo biloba* L., 3 kg of bark of *Cinnmomum cassia* Presl, 4 kg of licorice and 6 kg of twig of *Cinnmomum cassia* Presl were crushed into powder. The powder was then encapsulated according to methods known to those of skill in the art.

Experimental Example 1

The effect of anti-prostate hyperplasia medicaments and the composition of the present invention in rats on prostate hyperplasia caused by testosterone propionate was evaluated as discussed below.

Experimental Materials

Medicaments:
1. PROSCAR (5-α-reductase inhibitor): tablets, produced by Merck & Co., Inc., (UK) Co., prepared as 0.5 mg/ml medicament.
2. Saw Palmetto tablets, produced by Zhejiang Conba Pharmaceutical Co. Ltd., prepared with distilled water into 0.5 mg/ml medical liquid.
3. Longbishu Capsules: produced by SHIJIAZHUAN KEDI Pharmaceutical Co., Ltd., prepared with distilled water into 0.18 g/ml medical liquid.
4. The final extract of Example 9, prepared into 6 g/ml medical liquid.
5. Estradiol Benzoate injection
6. Testosterone propionate injection Test Method and Results Six 130 g-150 g male Wistar rats were anaesthetized with ether. The testes of each rat were removed under axenic conditions, and the test rats were bred for a week after operation. The rats were divided at random into 6 groups, with 6 rats in each group. All groups of animals were hyped each day with 5 mg/Kg testosterone propionate dissolved in prepared peanut oil. The control (contrast) groups were administered a physiological salt solution. The test groups were administered a treatment of 5 mg/Kg PROSCAR, 5 g/Kg Saw Palmetto, 1.8 g/Kg longbishu, and 6 g/Kg of the final extract obtained in Example 9 The treatment took the form of a1 ml/100 g medicament; for hypodermic injections of 50 μg/Kg estradiol benzoate, the volume was 0.05 ml/Kg, administered once a day for 30 days. 24 hours after the final treatment, all the rats were killed. The whole prostate glands were anatomized and placed in formalin. Extraneous fat was cut away from the prostate glands and the liquid on the surface was dried with filter papers. The prostate glands were then weighed with a tissue balance to calculate the weight. Table 1 shows the results:

Sixty (60) 18-22 g male mice were selected and randomly divided into 6 groups of 10 mice: a control (contrast) group administered physiological salt solution, a group administered hydrocortisone, a group administered Saw Palmetto, and three groups administered different dosages (1.5, 3.0 and 6.0 g/kg) of the extract from Example 9. The treatments were administered to the mice once a day for 5 days. After the last treatment, 0.05 ml of a mixed inflammatory solution of croton oil (2% croton oil, 20% anhydrous ethanol, 5% distilled water and 73% ether) was applied to the front and rear sides of the left ears of the animals. Four hours after inflammation, the mice were killed with a disjointed cervical vertebra method. The two ears were cut along the auricle baseline. Equal parts of the two ears (by area) were cut off and weighed on weighing scales to test twisting force. The degree of swelling/inflammation was obtained by subtracting the weight of the right ear from the weight of the left ear. The degrees of swelling between the control (contrast) groups and the test groups were analyzed statistically and the swelling inhibition rate was obtained. Table 2 shows the results:

TABLE 1

Impact on Prostate Gland Factors (mg/100 g) of Rats by medicaments of antiprostate hyperplasia, x ± SD

| Medicament | Dosage/volume g/kg weight g/kg | Number of animals | Anterior lobe | Inhibition rate % | Sum of three lobes (anterior, head and posterior lobes) | Inhibition rate % |
|---|---|---|---|---|---|---|
| Contrast group | — | 10 | 284.7 ± 75.7 | | 721.2 ± 129.7 | |
| estradiol benzoate | 50 g/Kg | 10 | 180.1 ± 55.8 | 36.7** | 585.3 ± 80.5 | 18.8** |
| PROSCAR | 5 mg/Kg | 10 | 164.2 ± 31.4 | 42.3** | 453.4 ± 59.1 | 37.1** |
| Saw Palmetto | 5 g/Kg | 10 | 250.6 ± 40.9 | 11.9** | 656.5 ± 88.1 | 4.7** |
| Longbishu | 1.8 g/Kg | 10 | 231.4 ± 37.0 | 18.7** | 650.2 ± 68.1 | 9.8** |
| The extract | 6 g(crude drug)/Kg | 10 | 190.2 ± 30.3 | 33.2** | 497.9 ± 81.1 | 30.9** |

Note:
compared with the contrast groups *P < 0.05, **P < 0.01

Experimental Example 2

Study on the Action of Anti-Prostate Hyperplasia by the Extract of the Present Invention The anti-inflammatory impact action of the extract of the present invention on testosterone propionate-induced prostate hyperplasia was observed in order to evaluate its efficacy.

Experimental Materials
1. Animals.
   a) Wistar rats;
   b) mice of Kunming origin.
2. Medicaments:
   a) The extract obtained in Example 9;
   b) Estradiol benzoate injection;
   c) Testosterone Propionate injection;
   d) Hydrocortisone acetate injection.

Experimental Method and Results:
1. Impact on Otic Swelling Caused by Mixed Inflammatory Solution of Croton Oil.

TABLE 2

Impact on otic swelling degrees caused by mixed inflammatory solution of croton oil by the extract in this Invention

| Groups | Dosage | Number of animals | Swelling degree (mg) (x ± SD) | P | Inhabitation rate % |
|---|---|---|---|---|---|
| Contrast group | | 10 | 17.85 ± 2.05 | | |
| The said extract | 1.5 g/kg | 10 | 15.25 ± 2.26 | <0.05 | 14.56 |
| The said extract | 3 g/kg | 10 | 13.10 ± 1.45 | <0.01 | 26.61 |
| The said extract | 6 g/kg | 10 | 11.55 ± 2.38 | <0.01 | 35.29 |
| Saw Palmetto | 2.5 g/kg | 10 | 12.65 ± 1.30 | <0.01 | 29.13 |
| Hydrocortisone | 20 mg/kg | 10 | 9.50 ± 2.93 | <0.01 | 46.77 |

These results show that the high, middle and low dosages of the extract of the present invention all reduce the degree of swelling of mouse otic inflammation caused by the mixed inflammatory solution of croton oil. Therefore, the extract of the present invention has anti-inflammatory properties.

Experimental Example 3

Impact on Permeability of Mice Celiac Capillary Vessels

The same experimental materials and animals as in Experimental Example 2 were used. However, the animals were not randomly assigned to groups. Rather, that the sixty (60) 18-22 g male mice were selected and divided into 6 groups according to weight, 10 in each group: a control (contrast) group administered a physiological salt solution, a group administered hydrocortisone, a group administered Saw Palmetto, and three dosage (1.5, 3.0 and 6.0 g/kg) groups of the extract obtained in Example 9. The treatments were administered once a day for 5 days. One hour after the last treatment, the mice were intravenously injected with 5 ml/kg of 0.5% Evans blue. After 5 minutes, 10 mil/mg of 0.7% acetic acid were injected into the abdomens of the mice. After 30 minutes, the mice were killed via a disjointed cervical vertebra method. The abdomens were washed several times with distilled water. The washing solution was then administered in a total amount of 10 ml/mg, and 0.1N NaOH 0.1 mL was added. After the solution was in place for 30 minutes, the light density of mice celiac transudate was measured with a colorimetry of a 721 spectrophotometer. Table 3 shows the results:

TABLE 3 impact on permeability of capillary vessels by the extract in this Invention

| Groups | Dosage | Number of animals | Evans blue transudate (OD x ± SD) | P | Inhibition rate (%) |
|---|---|---|---|---|---|
| Contrast | | 10 | 0.166 ± 0.04 | | |
| The said extract | 1.5 g/kg | 10 | 0.133 ± 0.030 | >0.05 | 19.87 |
| The said extract | 3 g/kg | 10 | 0.117 ± 0.031 | <0.01 | 29.52 |
| The said extract | 6 g/kg | 10 | 0.100 ± 0.027 | <0.01 | 39.75 |
| Saw Palmetto | 2.5 g/kg | 10 | 0.122 ± 0.033 | <0.05 | 26.51 |
| Hydrocortisone | 20 mg/kg | 10 | 0.092 ± 0.019 | <0.01 | 44.58 |

These results show that the high, middle and low dosages of the extract of the present invention all reduce the permeability of mice celiac capillary vessels and make the Evans blue transudate decline. Therefore, the extract in of the present invention has anti-inflammatory properties.

Experimental Example 4

Impact on Tampon Granuloma of Rats

The same experimental materials and animals as in Experimental Example 2 were used. However, sixty (60) 150-180 g male rats were used. Under ether anesthesia and normal disinfection, two±1 mg sterilized tampons were embedded under the inguinal skins on either side of the bodies. On the day of the operation, the 60 rats were randomly divided into 6 groups, 10 rats per group: a control (contrast) group administered physiological salt solution, a group administered hydrocortisone, a group administered Saw Palmetto, and three dosage (1.5, 3.0 and 6.0 g/kg) groups administered the extract obtained in Example 9. The treatments were administered into the rats' stomachs once a day for 7 days. On the eighth day, the rats were killed via a disjointed cervical vertebra method. The tampons were removed and placed in a 60° C. oven for 12 hours and then weighed. Table 4 shows the results:

TABLE 4 impact on tampon granuloma of rats

| Groups | Dosage | Number of animals | Weight of tampon granuloma (mg x ± SD) | P | Inhibition rate % |
|---|---|---|---|---|---|
| Contrast | | 10 | 45.95 ± 9.03 | | |
| The said extract | 1.5 g/kg | 10 | 40.30 ± 7.32 | >0.05 | 12.30 |
| The said extract | 3 g/kg | 10 | 38.05 ± 6.17 | <0.05 | 17.19 |
| The said extract | 6 g/kg | 10 | 32.15 ± 5.41 | <0.01 | 30.03 |
| Saw Palmetto | 2.5 g/kg | 10 | 42.30 ± 6.36 | >0.05 | 7.94 |
| Hydrocortisone | 20 mg/kg | 10 | 26.45 ± 2.61 | <0.01 | 42.43 |

These results show that the high and middle dosages of the extract of the present invention inhibit the hyperplasia of tampon granuloma of rats. Therefore, the extract of the present invention has anti-inflammatory properties.

Experimental Example 5

Impact on Testosterone Propionate-Induced Prostate Hyperplasia in Rats

The same experimental materials and animals as in Experimental Example 2 were used. However, fifty (50) 130-150 g male Wistar rats were used. Under ether anesthesia and in sterilized surroundings, both testes of each rat were removed. The rats were then bred for a week after the operation. Next, the rats were randomly divided into 5 groups of 10 rats each. Each group of animals were hyped with 5 mg/kg testosterone propionate dissolved in prepared oil once a day. During the same time period, each group was also given one of the treatments: the control (contrast) group was administered a physiological saline solution; three test groups were administered a dose (1.5, 3 and 6 g/kg) of the extract from Example 9 in a preparation of 1 m/100 g. The positive control (contrast) group was hyped with 50 µg/kg estradiol benzoate in a volume of 0.05 ml/100 g, once a day for 30 days. After the last treatment, the rats were killed and their whole prostate glands were anatomized. The prostate glands were placed in formalin. All the fat was cut away from the prostate glands after they were removed from the formalin. The remaining formalin on the prostate gland surface was dried with filter papers. The prostate glands were then placed in 70% ethanol and fixed for 24 hours. Next, the prostate glands were removed from the ethanol and placed on filter papers. The anterior, head and posterior lobes of the prostate glands were separated and weighed on a weighing scale to test twisting force. The transverse diameter, diameter and height of the anterior lobes of the prostate glands were measured with a two-foot vernier. The volume of the anterior lobe of a prostate gland was obtained by multiplying the values of the three measurements. Finally, the anterior lobes were examined with tectology, and the diameter of the prostate gland cavity and the height of the glandular epithelium cells were measured. Non-pairing t-examinations among the groups were conducted for all indexes. The values of the treatment groups were compared to the control (contrast) groups in order to determine the average difference. Table 5 and 6 show the results:

1. Impact on Weight of Prostate Glands of Rats 30 days after treatment, in comparison with the control (contrast) group, the 1.5 g, 3 g and 6 g crude drug/kg doses of the extract of the present invention demonstrated inhibition rates of 23.2% (P<0.01), 31.26% (P<0.01), and 34.46% (P<0.01) for prostate anterior lobe, respectively, and the inhibition rate of estradiol was demonstrated to be 35.3% (P<0.01); the inhibition rates for head lobes for the 1.5 g, 3 g and 6 g doses were 13.5%, 36.5% (P<0.01), and 46.0% (P<0.01), respectively, and the inhibition rate of estradiol was demonstrated to be 30.2% (P<0.05); the inhibition rates for posterior lobe for the 1.5 g, 3 g and 6 g doses were 9.6%, 15.3%, and 20.8%, respectively, and the inhibition rate of estradiol was 12.5%. These results show that the extract of the present invention inhibits the weight of the anterior and head lobes of the prostate gland but does not seem to influence the weight of the posterior lobe.

2. Impact on the Volume of Prostate Anterior Lobe of Rats

3. Impact on the Diameter of the Prostate Gland Cavity and on the Height of Glandular Epithelium Cells of Rats 30 days after treatment, microscopic examination has showed that the prostate gland body of the anterior, head and posterior lobes had obvious hyperplasia with enlarged acinus. There were also epithelioid papillas going into the gland cavity. Active excretion could also be seen on the hyperplastic glandular epithelium. The glandular epithelium cells appeared in high column-form or multi-layer form without clear cell boundaries. Additionally, the nucleus was placed on the base with parts of cell plasm in a grain form, and the glandular cavity was full of secretion. Hyperplasia of connective tissue between acini was also observed.

The histological changes in the treatment groups were nearly identical. The hyperplasia of the anterior and head glandular bodies were not as obvious as in the control (contrast) group. The hyperplasia of the posterior lobe was observed to have pathologic changes similar to the control (contrast) group. The extract of the present invention inhibits hyperplasia of the diameter of the glandular cavity of both the prostate anterior and head lobes. Estradiol also was shown to

TABLE 5

Impact on rat prostate factors (mg/100 g) of all lobes by the extract in this invention x ± SD

| Groups | Dosage (g/Kg body weight) | Number of animals | Anterior lobe | Head lobe | Rear lobe |
|---|---|---|---|---|---|
| Contrast | | 10 | 196.7 ± 41.1 | 73.4 ± 22.3 | 54.1 ± 12.8 |
| The said extract | 1.5 g/kg | 10 | 151.0 ± 28.1** | 63.5 ± 7.3 | 48.9 ± 11.9 |
| The said extract | 3.0 g/kg | 10 | 135.2 ± 40.9** | 46.6 ± 16.5** | 45.8 ± 15.3 |
| The said extract | 6.0 g/kg | 10 | 128.9 ± 26.3** | 39.6 ± 13.5** | 42.7 ± 12.3 |
| Estradiol benzoate | 50 μg/kg | 10 | 127.2 ± 23.4** | 51.2 ± 10.7* | 47.3 −+ 14.4 |

Note:
in comparison with the control (contrast) group: *P < 0.05, **P < 0.01

30 days after treatment, in comparison with the control (contrast) group, the groups administered the 1.5 g, 3 g and 6 g of crude drug/kg doses of the extract of the present invention demonstrated inhibition rates of 18.2%, 31.1% (P<0.01), and 40.3% (P<0.01), respectively, and the inhibition rate of estradiol was demonstrated to be 45.5% (P<0.01). These results show that the extract of the present invention inhibits the volume of the prostate gland.

TABLE 6

Impact on the volume of prostate anterior lobe of rats by the extract in this invention X ± SD

| Medicament | Dosage (g/kg weight) | Number of animals | Volume of anterior lobe (cm3) |
|---|---|---|---|
| Contrast group | | 10 | 0.77 ± 0.21 |
| The said extract | 1.5 g/kg | 10 | 0.63 ± 0.17 |
| The said extract | 3.0 g/kg | 10 | 0.53 ± 0.13** |
| The said extract | 6.0 g/kg | 10 | 0.46 ± 0.13** |
| Estradiol | 50 μg/kg | 10 | 0.42 ± 0.12** |

Note:
in comparison with the control (contrast) group: *P < 0.05, **P < 0.01 inhibit hyperplasia of the diameter of both the prostate anterior and head glandular cavities. In all groups, no influence was observed on the diameter of the posterior glandular cavity or on the height of the glandular epithelium cells in all the lobes. The results show that the extract of the present invention inhibits hyperplasia of the diameter of both the prostate anterior and head glandular cavities.

Experimental Example 6

Impact on Prostate Hyperplasia Caused by Implantation of Urine Genital Sinus of Mice Sixty (60) 30-35 g male mice, aged 7-10 weeks, were injected with celiac anesthesia with 50 mg/kg pentobarbital. The inferior belly was then cut open and the prostate gland was separated. A small hole was made in the celiac prostate gland with a needle. Next, three urine genital sinus tissues with a 16-day fetal age were implanted in the celiac anterior lobe of each prostate gland. The celiac prostate gland of 10 other mice were probed twice with an empty needle in order to create a blank control (contrast). The bellies of all the mice were then sutured. On the same day, the 60 animals were divided into 6 groups of 10 mice each: a blank control (contrast) group, a control (contrast) group, three dosage groups that were administered doses of the extract from Example 9, and a positive control (contrast) that was administered Saw Palmetto. The treatments were administered to the mice once a day for 30 days. After the last treatment, the mice were killed and paunched. The prostate glands were then removed and weighed with a tissue scale. The results were used to determine the differences between the treatment groups and the control (contrast) groups using the t-examination method. The rate of inhibition was also calculated. Table 7 shows the results:

TABLE 7

Impact on prostate hyperplasia caused by implantation of urine genital sinus of mice by the extract in this invention

| Groups | Dosage | Number of animals | Weight of prostate gland (mg/10 g x ± SD) | P | Inhibition rate % |
|---|---|---|---|---|---|
| Blank contrast | | 10 | 17.9 ± 6.32 | | |
| Contrast | | 10 | 63.4 ± 11.4 | | |
| The said extract | 1.5 g/kg | 10 | 53 ± 7.4 | <0.05 | 16.4 |
| The said extract | 3 g/kg | 10 | 45.8 ± 4.8 | <0.01 | 27.8 |
| The said extract | 6 g/kg | 10 | 41 ± 6.6 | <0.01 | 35.3 |
| Saw Palmett | 2.5 g/kg | 10 | 49.6 ± 8.6 | <0.01 | 21.8 |

The experimental results show that prostate hyperplasia is caused by implantation of urine genital sinus tissues of mice. 30 days after the mice took the extract of the present invention, the high, middle and low dosage groups showed reduced weight of the prostate glands. It was shown that the extract of the present invention inhibits prostate hyperplasia caused by the implantation of urine genital sinus tissues of mice.

Experimental Example 7

Curative Effect on Senile BPH Patients with the Extract in this Invention

Method:

In June-August 2002, 46 patients suffering from BPH (aged 51-70) were treated with the extract of Example 4. The treatment consisted of a 1.0 g tablet taken on an empty stomach with warm water in both the morning and the evening. The patients were treated and observed for one week and four weeks.

Results

Subjective symptoms were improved. The internal prostate symptom score ("IPSS") was reduced by an average of 16.6% after one week and by an average of 30% after four weeks. The maximum flow rate ("MFR") was increased by an average of 14.2% after one week and by an average of 33% after four weeks. The average post-void residual urine was reduced by 36% after four weeks of treatment, according to measurements taken with B-mode ultrasonagraphy. The extract of the present invention had no impact on pulse or blood pressure.

CONCLUSION

The extract of the present invention is safe and effective for treatment of elderly, senile BPH patients. It improves subjective and objective symptoms as well as improves quality of life without serious side effects.

1. Data and Methods 1.1 Clinical Data 46 male patients between the ages of 51-78, (average age of 63.2) were diagnosed as suffering from dysuria after having a digital rectal examination, examination with B-mode ultrasonic, etc. The causes of the dysuria included diseases such as sclerosis of neurogenic urinary bladder and the neck of bladder, carcinoma of the prostate, etc. and other diseases that have an impact on emiction. In accordance with the clinical diagnose, these males were diagnosed as suffering from BPH: IPSS>22 on average; MFR=10.6 ml/s (one urine volume>152 ml); and post-void residual urine volume=51.6 ml on average (as determined by ultrasound).

1.2 Treatment Methods 2 weeks prior to treatment, the patients were prohibited from ingesting diuretics. During treatment, each patient was treated with the extract of the present invention, in tablet form, twice a day and were instructed to cease ingesting any other BPH or emiction-disorder medicines. The patients ingested the tablets with warm water in the morning and evening on an empty stomach. The patients were treated and observed for one week and four weeks. Before the treatment and 1 week and 4 weeks after treatment, IPSS, urine flow rate, post-void residual urine, pulse and blood pressure were all measured separately. The side effects were also recorded. The examination and evaluation were analyzed with the t-check statistics.

2. Results 2.1 IPSS Evaluation

The average IPSS values before treatment, after one week of treatment, and after four weeks of treatment were, respectively, 24.6±3.4, 20.5±3.2, 17.2±4.1. The IPSS values decreased after treatment (P<0.01), the IPSS being reduced by 16.6% after one week of treatment and by 30% after four weeks of treatment. Table 8 shows the results.

2.2 Maximum Flow Rate (MFR)

The average MFR values before treatment, after one week of treatment and after four weeks of treatment were, respectively, (10.6±4.1) ml/s, (12.1±4.4) ml/s, and (14.1±3.8) ml/s. The MFR values increased after treatment (P<0.01), the MFR being increased by 14.2% after one week of treatment and by 33% after four weeks of treatment. Table 8 shows the results.

2.3 Post-Void Residual Urine

The average amount of post-void residual urine remaining in the bladder was measured (by celiac measurement with B-mode ultrasound) before treatment, after one week of treatment, and after four weeks of treatment These values were, respectively, (51.6±38) ml, (41±32) ml, and (33±26) ml. The values decreased after treatment (P<0.01), and the average post-void residual urine was reduced by 20.5% after one week of treatment and by 36% after four weeks of treatment. Table 8 shows the results.

2.4 Side Effects

No changes in pulse or blood pressure were observed between just prior to the treatment and after either one or four weeks of treatment.

TABLE 8

Comparison of improved urine flow before and after taking the extract of the present invention

| Time | Before treatment | 1 week after treatment | 4 weeks after treatment | P |
|---|---|---|---|---|
| IPSS value | 24.6 ± 3.4 | 20.5 ± 3.2 (↓16.6%) | 17.2 ± 4.1 (↓30%) | <0.01 |
| MFR(ml/s) | 10.6 ± 4.1 | 12.1 ± 4.4 (↑14.2%) | 14.1 ± 3.8 (↑33%) | <0.01 |
| Post-void residual urine (ml) | 51.6 ± 38 | 41 ± 32 (↓20.5%) | 33 ± 26 (↓36%) | <0.01 |

3. Discussion

According to traditional Chinese medicine, emiction disorders caused by BPH belong to the disease categories of dysuria and blockage. "Dysuria" refers to difficulty in urination, a slim and fragile urine line and blocked urine. When urination occurs with a degree of difficultly, it is referred to as "dysuria". When urination cannot occur, it is referred to as being blocked (i.e., the patient is suffering from "blockage"). By combining traditional Chinese medicine with modern medicine, a treatment for BPH has been created that is based on plant extracts. The treatment is for the improvement of emiction disorders caused by BPH. The treatment is safe and has a strong, quick-acting curative effect, sometimes taking as little as one week before the effects are experienced.

The clinical experiments have shown that the extract of the present invention can improve the symptoms of elderly and senile patients suffering from BPH due to the extract's strong immediate curative effect. After one week of treatment, a patient's IPSS can be reduced by, on average, 16.6%; a patient's MFR can be increased by, on average, 14.2%; and a patient's post-void residual urine volume can be reduced by, on average, 20.5%. Beneficially, side effects occur very rarely.

The invention claimed is:

1. An orally ingestible pharmaceutical composition for treating emiction disorders caused by benign prostate hyperplasia, consisting essentially of 9-45 parts by weight of Ginseng root (the root of *Panax ginseng* C. A. Mey), 20-100 parts by weight of core of Ginkgo (the seed of *Ginkgo biloba* L.), 2-30 parts by weight of Cinnamon (the bark of *Cinnamomum cassia* Presl) and 2-10 parts by weight of licorice (the root of *Glycyrrhiza uralensis* Fisch), said parts by weight being measured relative to each other.

2. An orally ingestible pharmaceutical composition for treating emiction disorders caused by benign prostate hyperplasia, consisting essentially of 9-45 parts by weight of Ginseng root (the root of *Panax ginseng* C. A. Mey) 20-100 parts by weight of core of Ginkgo (the seed of *Ginkgo biloba* L.), 2-30 parts by weight of Cinnamon (the bark of *Cinnamomum cassia* Presl), 2-10 parts by weight of licorice (the root of *Glycyrrhiza uralensis* Fisch), and 12 parts by weight of Cassia Twig (the twig of *Cinnamomum cassia* Presl), said parts by weight being measured relative to each other.

3. The orally ingestible pharmaceutical composition for treating emiction disorders caused by benign prostate hyperplasia of claim 1 or 2, further comprising pharmaceutically acceptable carriers.

4. The orally ingestible pharmaceutical composition for treating emiction disorders caused by benign prostate hyperplasia of claim 1 further characterized by that the composition is processed as powder, capsules or tablets.

5. The orally ingestible pharmaceutical composition for treating emiction disorders caused by benign prostate hyperplasia of claim 2 characterized by that the composition is processed as powder, capsules or tablets.

6. The orally ingestible pharmaceutical composition for treating emiction disorders caused by benign prostate hyperplasia of claim 1 or 2 further characterized by that the said composition is used in or as food.

* * * * *